(12) United States Patent
Krichevsky

(10) Patent No.: US 8,747,835 B1
(45) Date of Patent: *Jun. 10, 2014

(54) ARTIFICIAL AND MUTATED NUCLEOTIDE SEQUENCES

(71) Applicant: BioGlow LLC, St. Louis, MO (US)

(72) Inventor: Alexander Krichevsky, St. Louis, MO (US)

(73) Assignee: BioGlow, LLC, Saint Louis, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/901,339

(22) Filed: May 23, 2013

Related U.S. Application Data

(63) Continuation of application No. 13/800,840, filed on Mar. 13, 2013.

(51) Int. Cl.
*C12N 15/52* (2006.01)
*C12N 15/00* (2006.01)
*C12N 15/82* (2006.01)

(52) U.S. Cl.
USPC .......................... 424/93.2; 536/23.2; 435/419

(58) Field of Classification Search
None
See application file for complete search history.

(56) References Cited

U.S. PATENT DOCUMENTS

| | | | |
|---|---|---|---|
| 7,663,022 B1 | 2/2010 | Hudkins | |
| 2010/0192262 A1* | 7/2010 | Krichevsky | 800/298 |

FOREIGN PATENT DOCUMENTS

| | | |
|---|---|---|
| WO | 2009/017821 | 2/2009 |
| WO | 2011/106001 | 9/2011 |

OTHER PUBLICATIONS

Lee et al (1991, Eur. J. Biochem. 201:161-167).*
Ast et al (2007, J. Bacteriol. 189:6148-6158).*
Douglas S., (2008) "Basic Techniques for Propagating Plants", The Connecticut Agricultural Experiment Station, Department of Plant Pathology and Ecology.
Kooshki M., Mentewab A., Stewart N., (2003) "Pathogen inducible reporting in transgenic tobacco using a GFP construct", Plant Science, 165:213-19.
Krichevsky A., (2010) "Glowing Plants: The Next Big Opportunity?", Greenhouse Grower Magazine.
Krichevsky A., Meyers B., Vainstein A., Maliga P., Citovsky V., (2010) "Autoluminescent plants", PLoS One., 5(11): e15461.
Liu X., Germaine K.J., Ryan D., Dowling D.N., (2010) "Whole-cell fluorescent biosensors for bioavailability and biodegradation of polychlorinated biphenyls", Sensors (Basel), 10(2):1377-98.
Meighen E.A., (1993) "Bacterial bioluminescence: organization, regulation, and application of the lux genes", FASEB J., 7(11):1016-22.
Nakamura M., Sugiura M., (2007) "Translation efficiencies of synonymous codons are not always correlated with codon usage in tobacco chloroplasts", Plant J., 49(1):128-34.
Petushkov V.N., Lee J., (1997) "Purification and characterization of flavoproteins and cytochromes from the yellow bioluminescence marine bacterium Vibrio fischeri strain Y1", Eur. J. Biochem., 245(3):790-6.
Potera C., (2007) "Blooming biotech", Nat Biotechnol., 25(9):963-5.
Spyrou G., Haggard-Ljungquist E., Krook M., Jornvall H., Nilsson E., Reichard P., (1991) "Characterization of the flavin reductase gene (fre) of *Escherichia coli* and construction of a plasmid for overproduction of the enzyme" J Bacteriol.,173(12):3673-9.
Tian J., Ma K., Saaem I., (2009) "Advancing high-throughput gene synthesis technology", Mol. Biosyst., 5(7):714-22.

* cited by examiner

*Primary Examiner* — Anne Kubelik
(74) *Attorney, Agent, or Firm* — Dennis A. Bennett; Charles E. Cohen; Lauren L. Stevens

(57) ABSTRACT

The present invention relates to artificial nucleotide sequences, including specific mutations therein.

20 Claims, 2 Drawing Sheets

A

Pre-mutation  LuxC mut  Pre-mutation  LuxC mut 100 seconds exposure

B

LuxC mut  LuxC+E mut  LuxC mut  LuxC+E mut 10 seconds exposure

ARTIFICIAL AND MUTATED NUCLEOTIDE SEQUENCES

BACKGROUND OF THE INVENTION

1. Field of the Invention

Artificial and synthetic DNA sequences have gained extensive use with development of the field of synthetic biology in the past decade. The present invention relates to use of artificial nucleotide sequences in the field of bioluminescence, which is emission of light by living organisms. Bioluminescence of bacterial organisms is mediated by the bacterial LUX operon. The LUX operon encodes for the bacterial luciferase, the light emitting enzyme, as well as enzymes responsible for synthesis of luciferins, substrates required for the light emission reaction. The operon contains genes named C-D-A-B-E(-G), where Lux A and Lux B code for the components of the luciferase and Lux C, D and E code for a fatty acid reductase complex producing an aldehyde necessary for the reaction. LuxG codes for an enzyme thought to participate in the turnover of the second luciferin, the flavin mononucleotide.

2. Description of Related Art

In biotechnology, genes of the LUX operon have a wide range of applications. For instance, the LUX operon is utilized as a reporter in a variety of bacterial and plant biosensors. Bacterial cells of naturally non-glowing species such as *E. coli* have been engineered to contain the LUX operon inducible by pre-determined classes of chemicals. These cells start glowing in the presence of these specific compounds, reporting on the composition or toxicity of the sample. Plants engineered with a fully functional LUX operon have been contemplated for use as phytosensors, monitoring the conditions of the plant and the environment. Furthermore, ornamental plants have been engineered to contain a LUX operon to produce novel and unique types of glowing ornamental plants. The U.S. ornamentals market was sized at approximately $21B in the early 2000's, and the entire worldwide market for ornamental plants has been estimated to be over $100B.

The ornamental plant market is driven by innovation, where outdated varieties are inevitably replaced by new types of plants and flowers. New colors of roses and carnations, and new shapes and colors of petunias, find their way to the marketplace every year. Generation of new and esthetically pleasing varieties is known to be the key force driving the floriculture industry and stimulating its growth.

However, one of the major limitations of the applicability of LUX operon-based technologies, particularly in plants, is low levels of light emission in plants expressing LUX genes. Therefore means to engineer the LUX operon to enhance and augment plant light emission are needed.

The present invention addresses this problem, and provides several means of enhancing light emission, instrumental in producing new, exciting varieties of highly autoluminescent ornamental plants, as well as additional plant products, such as more effective autoluminescent plant phytosensors.

SUMMARY OF THE INVENTION

The present invention discloses novel artificial DNA sequences, i.e., SEQ ID NOs:1-8 and 11-12, shown in the section entitled "Nucleotide and Amino Acid Sequences of the Invention", variously encoding for LUX and other polypeptides, useful in enhancing autoluminescence.

In another aspect, the present invention discloses specific mutations in the LuxC and LuxE genes that are highly effective in enhancing light emission in an organism, such as a bacterium or plant, containing these genes in a mutated LUX operon.

More specifically, in its various aspects, the present invention provides:

[1] A nucleic acid construct, comprising the nucleotide sequences shown in SEQ ID NOs: 1-5, operably linked for expression.

[2] A nucleic acid construct, comprising the nucleotide sequences shown in SEQ ID NOs: 1-6, operably linked for expression.

[3] The nucleic acid construct of [1] or [2], further comprising, operably linked for expression, the nucleotide sequence shown in SEQ ID NO:7.

[4] The nucleic acid construct of any one of [1]-[3], further comprising, operably linked for expression, the nucleotide sequence shown in SEQ ID NO:8.

[5] The nucleic acid construct of any one of [1]-[4], which is an expression cassette.

[6] An expression vector, comprising the expression cassette of [5].

[7] A living cell, containing any one or more of the nucleotide sequences shown in SEQ ID NOs:1-8 or 11-12.

[8] The living cell of [7], containing the nucleotide sequences shown in SEQ ID NOs:1-5, operably linked for expression.

[9] The living cell of [7], containing the nucleotide sequences shown in SEQ ID NOs: 1-6, operably linked for expression.

[10] The living cell of [8], further comprising at least one nucleotide sequence selected from the group consisting of SEQ ID NO:7 and SEQ ID NO:8, operably linked for expression.

[11] The living con of [9], further comprising at least one nucleotide sequence selected from the group consisting of SEQ ID NO:7 and SEQ ID NO:8, operably linked for expression.

[12] The living cell of any one of [7]-[11], which is selected from the group consisting of a bacterial cell and a plant cell.

[13] The living cell of [12], which is autoluminescent.

[14] A plant, a cell of which contains said nucleic acid construct, expression cassette, expression vector, or nucleotide sequences of any one of [1]-[6].

[15] The plant of [14], wherein said nucleic acid construct, expression cassette, expression vector, or nucleotide sequences are located in a plastid.

[16] The plant of [15], wherein the plastid is a chloroplast.

[17] The plant of any one of [14]-[16], wherein said nucleotide sequences are expressed.

[18] The plant of [17], which is autoluminescent.

[19] Progeny of the plant of [18].

[20] The progeny of [19], which are produced sexually or asexually.

[21] The progeny of [20], which are produced asexually from cuttings.

[22] A part of said plant or progeny of any one of [14]-[21].

[23] The part of said plant or progeny of [22], which is selected from the group consisting of a protoplast, a cell, a tissue, an organ, a cutting, and an explant.

[24] The part of said plant or progeny of [22], which is selected from the group consisting of an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

[25] A method of producing an autoluminescent plant, comprising asexually propagating a cutting of said plant or progeny of any one of [14]-[21].

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed description taken in conjunction with the accompanying drawings, all of which are given by way of illustration only, and are not limitative of the present invention, in which.

NUCLEOTIDE AND AMINO ACID SEQUENCES

Figure 1:
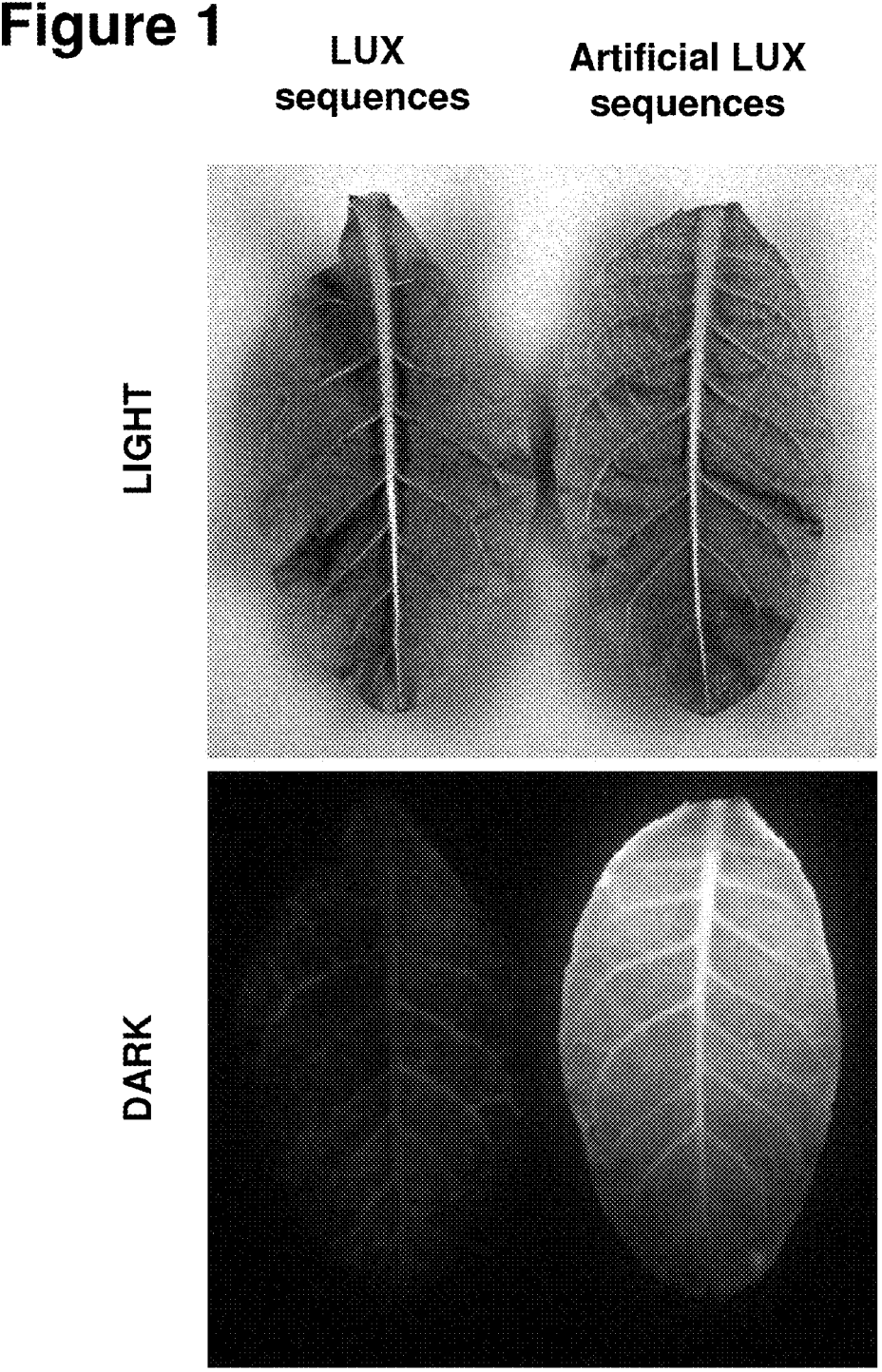
FIG. 1 shows an example of enhanced light output of transgenic autoluminescent tobacco containing a combination of artificial LUX sequences SEQ ID NOs:1, 2, 11, 4, 12, and 6 (right panel) vs. autoluminescent tobacco plants containing known wild-type LUX sequences (left panel). Light emission is detected using a ChemiDoc XRS Molecular Imager; inverse images are shown.

SEQ ID NO:1: artificial Lux A nucleotide sequence;
SEQ ID NO:2: artificial Lux B nucleotide sequence;
SEQ ID NO:3: artificial Lux C nucleotide sequence, incorporating Ala Gly mutation at amino acid position 389;
SEQ ID NO:4: artificial Lux D nucleotide sequence;
SEQ ID NO:5: artificial Lux E nucleotide sequence, incorporating Gln Glu mutation at amino acid position 167;
SEQ ID NO:6: artificial Lux G nucleotide sequence;
SEQ ID NO:7: artificial *E. coli* Fre nucleotide sequence;
SEQ ID NO:8: artificial *V. fischeri* Yellow Fluorescent Protein nucleotide sequence;
SEQ ID NO:9: amino acid sequence of wild-type *Photobacterium leiognathi* LuxC protein;
SEQ ID NO:10: amino acid sequence of wild-type *Photobacterium leiognathi* LuxE protein;
SEQ ID NO:11: artificial Lux C nucleotide sequence without Ala→Gly mutation at amino acid position 389. Compare to SEQ ID NO:3;
SEQ ID NO:12: artificial Lux E nucleotide sequence without Gln→Glu mutation at amino acid position 167. Compare to SEQ ID NO:5.

Although not listed above, the present invention also encompasses the amino acid sequences of the proteins encoded by the nucleotide sequences listed. Such amino acid sequences can be deduced by, for example, conventional bioinformatics methods, including the use of publicly available and proprietary computer programs designed for this purpose.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein is herein incorporated by reference in its entirety.

Methods and techniques for generating transgenic, transplastomic, and otherwise genetically modified plants are well known in the art.

The use of native LUX genes to produce autoluminescent plants has been previously described in the art. Patent applications by Krichevsky, i.e., WO 2009/017821 and WO 2011/106001, disclose the use of naturally occurring LUX genes in the form of an operon in plastids, and U.S. Pat. No. 7,663,022 by Hudkins prophetically contemplates nuclear expression of LUX genes from separate vectors.

However, none of these references either discloses or suggests the artificial LUX, *E. coli* Fre, or *V. fischeri* Yellow Fluorescent Protein (YFP) sequences SEQ ID NOs:1-8 and 11-12 of the present invention. Further, the art does not teach or suggest the mutations in LuxC and LuxE genes disclosed herein.

In one embodiment, LUX operon genes are used in variety of biotechnology applications, which can further benefit from enhancement of light output generated by the LUX operon. For example, the problem of enhancing the light output of the autoluminescent plants disclosed in the above-noted PCT applications and producing brighter glowing plants, which are appealing and attractive to the consumer, is solved by the artificial DNA sequences of the present invention. Expression of these sequences, or combinations thereof, results in autoluminescent plants that are several fold brighter than plants expressing wild-type LUX genes.

Examples of certain preferred combinations of the artificial sequences disclosed herein include, but are not limited to: SEQ ID NOs:1-5 in combination; SEQ ID NOs:1-6 in combination; or further, combination of SEQ ID NOs:1-5 in combination or SEQ ID NOs:1-6 in combination, further in combination with SEQ ID NO:7; and further, such foregoing combinations, further in combination with SEQ ID NO:8. In each of these cases, the nucleotide sequences are operably linked for expression.

One skilled in the art will recognize that the individual sequences disclosed herein can be used in combination, as indicated above, in any order, and are independent of one another.

As used herein, the phrase "operably linked for expression" and the like encompasses nucleic acid sequences linked in the 5' to 3' direction in such a way as to facilitate expression of an included nucleotide coding sequence.

The following examples are meant to be illustrative, and not limiting, of the practice or products of the present invention.

Example 1

Enhanced Light Emission by a Combination of SEQ ID NOs:1, 2, 11, 4, 12, and 6

An example of light emission enhancement in transgenic tobacco by a combination of artificial sequences of the present invention, employing SEQ ID NOs: 1, 2, 11, 4, 12, and 6 operably linked for expression, compared to that produced by a combination of wild-type LUX operon genes C-D-A-B-E(-G) operably linked for expression, is shown in FIG. 1. The methods employed to produce these plants are disclosed in the inventor's PCT International Publications WO 2009/017821 and WO 2011/106001.

Artificial sequences SEQ ID NOs:7 and 8, encoding FRE and YFP proteins, respectively, are designed to further improve light output and change the emitted light color, respectively, of the autoluminescent plants encompassed by the present invention.

Example 2

Light Emission Enhancement by LUX Structural Gene Mutants

A number of mutations in the regulatory genes governing expression of the entire LUX operon in bacteria are known in the art. However, mutations in the LUX structural genes, and particularly in LuxC and LuxE, enhancing or otherwise modulating light emission generated by the LUX operon have not been previously identified.

Disclosed herein are two novel mutations in the structural LUX genes C (encoding an Ala→Gly mutation at amino acid position 389) and E (encoding a Gln→Glu mutation at amino acid position 167), which greatly enhance light emission of the LUX operon.

The known sequence of the *Photobacterium leiognathi* LUX operon (GeneBank #M63594) discloses the following sequences of the wild-type LuxC and LuxE genes:
LuxC (Gene Bank M63594) (SEQ ID NO:9)

MIKKIPMIIGGVVQNTSGYGMRELTLNNNKVNIPIITQSDVEAIQSLNIENKLTINQIVNFLYTVGQKW

KSETYSRRLTYIRDLIKFLGYSQEMAKLEANWISMILCSKSALYDIVENDLSSRHIIDEWIPQGECYVK

ALPKGKSVHLLAGNVPLSGVTSILRAILTKNECIIKTSSADPFTATALVNSFIDVDAEHPITRSISVMY

WSHSEDLAIPKQIMSCADVVIAWGGDDAIKWATEHAPSHADILKFGPKKSISIVDNPTDIKAAAIGVAH

DICFYDQQACFSTQDIYYIGDSIDIFFDELAQQLNKYKDILPKGERNFDEKAAFSLTERECLFAKYKVQ

KGESQSWLLTQSPAGSFGNQPLSRSAYIHQVNDISEVIPFVHK<u>A</u>VTQTVAIAPWESSFKYRDILAEHGA

ERIIEAGMNNIFRVGGAHDGMRPLQRLVNYISHERPSTYTTKDVSVKIEQTRYLEEDKFLVFVP

LuxE (Gene Bank M63594) (SEQ ID NO:10)

MSTLLNIDATEIKVSTEIDDIIFTSSPLTLLFEDQEKIQKELILESFHYHYNHNKDYKYYCNIQGVDEN

IQSIDDIPVFPTSMFKYSRLHTADESNIENWFTSSGTKGVKSHIARDRQSIERLLGSVNYGMKYLGEFH

EHQLELVNMGPDRFSASNVWFKYVMSLV<u>Q</u>LLYPTTFTVENDEIDFEQTILALKAIQRKGKGICLIGPPY

FIYLLCHYMKEHNIEFNAGAHMFIITGGGWKTKQKEALNRQDFNQLLMETFSLFHESQIRDIFNQVELN

TCFFEDSLQRKHVPPWVYARALDPVTLTPVEDGQEGLMSYMDASSTSYPTFIVTDDIGIVRHLKEPDPF

QGTTVEIVRRLNTREQKGCSLSMATSLK

As disclosed herein, substitution of Ala (position 389) in the amino acid sequence of LuxC (SEQ ID NO:9; emphasized in the sequence in 14 point type, bold, and underlined) with, for example Gly, strongly enhances light emission generated by the operon. Moreover, substitution of Gln (position 167) in the amino acid sequence of LuxE (SEQ ID NO:10; emphasized in the sequence in 14 point type, bold, and underlined) with, for example Glu, further increases light emission of *E. coli* harboring the mutated operons (FIG. 2).

Methods for nucleic acid mutagenesis are known in the art (e.g., Chen et al. (1997) "High efficiency of site-directed mutagenesis mediated by a single PCR product." *Nuc. Acid Res,* 25(3): 682-4). Methods for transforming *E. coli* are well known in the art.

Figure 2:
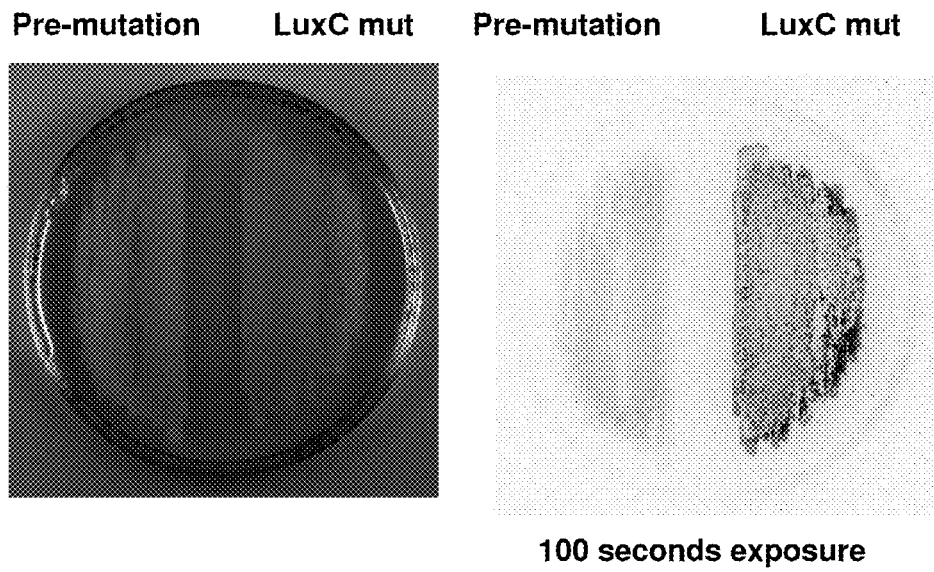
FIG. 2 shows the further effect of mutations in structural LUX genes in enhancing light emission of the LUX operon in *E. coli*. (A) Change of Ala to Gly in LuxC amino acid sequence position 389 (SEQ ID NO:3) enhances light emission; (B) Change of Gln to Glu in LuxE amino acid position 167 (SEQ ID NO:5) used in combination with SEQ ID NO:3 further enhances light emission compared to the use of SEQ ID NO:3 alone. *E. coli* cultures carrying the mutations imaged using ChemiDoc XRS Molecular Imager. Left panel: culture plates in light; right panel: photographic exposure of the cultures; 100 sec exposure for (A), 10 sec exposure for (B).
Figure 2:
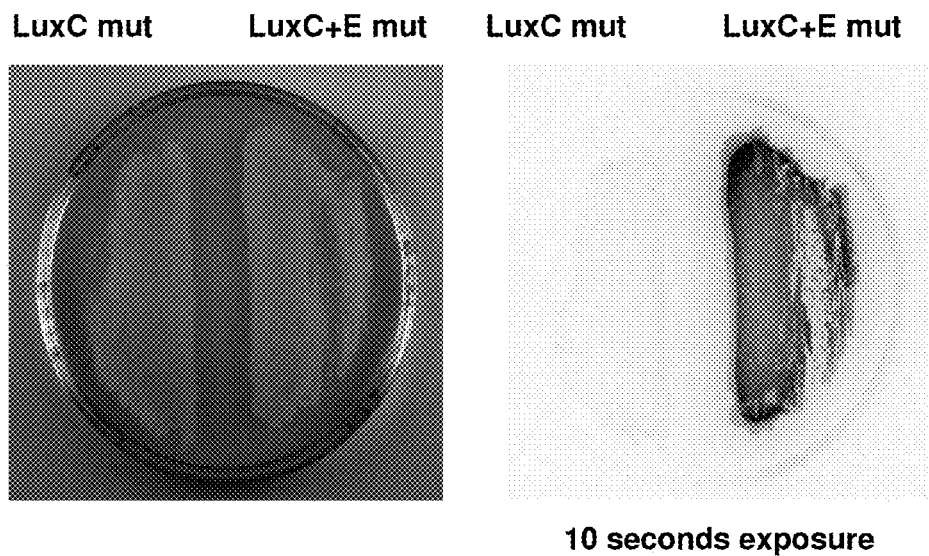

In the particular example shown in FIG. 2, the mutant LuxC gene (SEQ ID NO:3) is first introduced into the operon (SEQ ID NOs: 1-4, 12, and 6) introduced into the bacteria (Panel A), followed by introduction of the mutant LuxE gene (SEQ ID NO:5) into the operon (SEQ ID NOs:1-6) introduced into the bacteria (Panel B). One skilled in the art will appreciate that these mutations can be introduced in any order, and are independent of one another. Each mutation can be used for light emission enhancement separately, in combination with one another, or as indicated above, each can be used separately, or together, in combination with any other mutations or sequences. This includes, for example, the combinations listed above.

This example demonstrates the luminescence-enhancing effect of LuxC Ala (389) substitution to Gly and LuxE Gln (167) substitution to Glu in *E. coli*.

Specifically, FIG. 2 shows the further effect of mutations in these structural LUX genes in enhancing light emission of the LUX operon in *E. coli*. Panel (A) shows that change of Ala to Gly in LuxC amino acid sequence position 389 (SEQ ID NO:3) enhances bacterial light emission; Panel (B) shows that change of Gln to Glu in LuxE amino acid position 167 (SEQ ID NO:5), used in combination with SEQ ID NO:3, further enhances light emission compared to the use of SEQ ID NO:3 alone.

In view of these results, it is fully expected that use of artificial nucleotide sequences encoding LUXC comprising the Ala→Gly mutation, e.g., SEQ ID NO:3, and LUXE, comprising the Gln→Glu mutation, e.g., SEQ ID NO:5, either alone, or together, in combination with the other artificial LUX operon sequences disclosed herein, will produce a similar light-enhancing effect in plants.

As noted above, preferred combinations of the artificial sequences disclosed herein include, but are not limited to: SEQ ID NOs:1-5 in combination; SEQ ID NOs:1-6 in combination; or further, combination of SEQ ID NOs:1-5 in combination or SEQ ID NOs:1-6 in combination, further in combination with SEQ ID NO:7; and further, such foregoing combinations, further in combination with SEQ ID NO:8. In each of these cases, the nucleotide sequences are operably linked for expression.

One skilled in the art can appreciate that substitution of LuxC with other amino acids in position (389) and LuxE in position (167) can result in different modifications of light emission, which can be further used to modulate LUX operon luminescence. Furthermore, depending on the type of bacteria from which the LUX operon is derived, positions of these critical amino acids can be shifted within close proximity to the described residues of *P. leiognathi*, or located in sequences with high homology to sequences surrounding position (389) in LuxC and position (167) in LuxE.

The artificial DNA sequences of the present invention incorporate the above described LuxC and LuxE mutations (SEQ ID NOs:3 and 5, respectively), designed to further enhance light output of the LUX operon. The utility and applicability of the current invention includes, for example, generating bright autoluminescent plants. Besides applications in ornamental plants, where bright plants are attractive to consumers, the present sequences have utility in producing highly effective plant biosensors emitting light in response to various types of stress or other conditions when operons containing these sequences are under the control of appropriate promoters, e.g., stress-inducible promoters, and are thus useful in agriculture for crop or environmental monitoring.

Plants encompassed by the present invention include both monocots and dicots, ornamentals as well as crop plants. Non-limiting examples include ornamental plants such as petunias, poinsettias, and roses, as well as crop plants such as corn and oil producing palms.

Also encompassed by the present invention are parts of such plants including, for example, a protoplast, a cell, a tissue, an organ, a cutting, and an explant. Such parts further include an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus. The present invention also encompasses progeny, whether produced sexually or asexually, of transgsenic plants of the invention containing sequences disclosed herein.

In regard to methods of propagating autoluminescent plants encompassed by the present invention, methods of propagation and reproduction of such plants are well known in the art, and include both sexual and asexual techniques.

Asexual reproduction is the propagation of a plant to multiply the plant without the use of seeds to assure an exact genetic copy of the plant being reproduced.

Any known method of asexual reproduction which renders a true genetic copy of the plant may be employed in the present invention. Acceptable modes of asexual reproduction include, but are not limited to, rooting cuttings; grafting; explants; budding; apomictic seeds; bulbs; division; slips; layering; rhizomes; runners; corms; tissue culture; nucellar embryos; and any other conventional method of asexual propagation. The present invention encompasses all such methods of propagation and reproduction of plants encompassed by the present invention.

In additional examples, the presently disclosed DNA sequences are further useful in generating more efficient plant research systems, where their autoluminescent properties can be used as a reporter system for gene expression and other scientific assays.

The invention being thus described, it will be recognized that the same may be varied in many ways. Such variations are not to be regarded as a departure from the spirit and scope of the invention, and all such modifications as would be obvious to one skilled in the art are intended to be included within the scope of the following claims.

What is claimed is:

1. A nucleic acid construct, comprising the nucleotide sequences shown in SEQ ID NOs: 1-5, operably linked for expression.

2. A nucleic acid construct, comprising the nucleotide sequences shown in SEQ ID NOs:1-6, operably linked for expression.

3. The nucleic acid construct of claim 1, further comprising, operably linked for expression, the nucleotide sequence shown in SEQ ID NO:7.

4. The nucleic acid construct of claim 2, further comprising, operably linked for expression, the nucleotide sequence shown in SEQ ID NO:7.

5. The nucleic acid construct of claim 1, further comprising, operably linked for expression, the nucleotide sequence shown in SEQ ID NO:8.

6. The nucleic acid construct of claim 2, further comprising, operably linked for expression, the nucleotide sequence shown in SEQ ID NO:8.

7. The nucleic acid construct of claim 3, further comprising, operably linked for expression, the nucleotide sequence shown in SEQ ID NO:8.

8. The nucleic acid construct of claim 4, further comprising, operably linked for expression, the nucleotide sequence shown in SEQ ID NO:8.

9. The nucleic acid construct of claim 1, which is an expression cassette.

10. The nucleic acid construct of claim 2, which is an expression cassette.

11. The nucleic acid construct of claim 3, which is an expression cassette.

12. The nucleic acid construct of claim 4, which is an expression cassette.

13. The nucleic acid construct of claim 5, which is an expression cassette.

14. The nucleic acid construct of claim 6, which is an expression cassette.

15. The nucleic acid construct of claim 7, which is an expression cassette.

16. The nucleic acid construct of claim 8, which is an expression cassette.

17. A living cell, containing the nucleotide sequences shown in SEQ ID NOs:1-5, operably linked for expression.

18. The living cell of claim 17, comprising the nucleotide sequences shown in SEQ ID NOs:1-6, operably linked for expression.

19. The living cell of claim 17, further comprising at least one nucleotide sequence selected from the group consisting of SEQ ID NO:7 and SEQ ID NO:8, operably linked for expression.

20. The living cell of claim 18, further comprising at least one nucleotide sequence selected from the group consisting of SEQ ID NO:7 and SEQ ID NO:8, operably linked for expression.

* * * * *

SEQUENCE LISTING

```
<160> NUMBER OF SEQ ID NOS: 12

<210> SEQ ID NO 1
<211> LENGTH: 1065
<212> TYPE: DNA
<213> ORGANISM: Artificial Sequence
<220> FEATURE:
<223> OTHER INFORMATION: Synthesized

<400> SEQUENCE: 1
atgaaaataa gtaatatttg tttctcatat caaccaccag gggagtccca tcaggaggtt      60
atggaaaggt ttatacgact aggtgtcgca tctgaagaat taaattttga tggattttat     120
actttagagc accattttac cgaatttgga ataactggta atttatatat tgcatgtgca     180
aacatactag gacgaactaa gcgtattcaa gttggcacaa tgggcatagt tcttcctaca     240
gagcatccgg ctcgacatgt agaatcacta cttgttcttg atcaattgtc taagggtaga     300
tttaattatg gaacggttag gggtttgtat cataaggatt ttcgagtgtt tgggacatcc     360
caggaggatt cccgaaaaac agcagaaaat ttctattcta tgattttaga tgcgtccaag     420
accggagtgt tgcatacgga cggggaggta gtagaatttc ctgatgtgaa tgtctaccca     480
```

-continued gaagcctatt ctaaaaagca gcctacttgt atgactgcgg aatcttctga gactattact      540
tatttagcgg aaagagggct acctatggtg ttaagttgga ttatcccagt tagtgaaaaa      600
gtatctcaaa tggagttata taatgaagtg ccgctgaac atgggcatga tataaacaat       660
attgaacaca ttctaacatt tatttgctct gttaatgaag atggggagaa agccgatagt      720
gtatgtagga attttttgga gaattggtat gactcctaca agaatgccac aaacatcttt     780
aatgattcca accaaacaag aggttatgat tatttaaaag ctcaatggcg agagtgggtt     840
atgaaaggtt tagctgaccc acgaaggcgt cttgattatt ctaatgaatt aaatccggtc     900
ggtacacctg aacgttgtat cgaaattatt caaagtaata ttgatgcaac cgggataaaa    960
cacattaccg tgggctttga agctaatggt agtgaacagg aaattagaga atctatggaa    1020 cttttatgg aaaaagttgc accgcatctt aaagatcccc aataa                      1065

<210> SEQ ID NO 2
<211> LENGTH: 981
<212> TYPE: DNA
<213> ORGANISM: Artificial Sequence
<220> FEATURE:
<223> OTHER INFORMATION: Synthesized

<400> SEQUENCE: 2
atgaactttg gattgttttt cctaaatttc caaccagaag gaatgacttc cgaaatggta       60
ctagataata tggttgatac agtagcattg gtagacaaag atgactatca tttcaagcgt      120
gtattggtgt ctgaacatca tttctccaaa aatggcatta taggggagcc cttaaccgct     180
atatctttcc ttttaggtct aaccaagaga atagaaatag gttctttgaa tcaggttata     240
acgacccacc atcctgtaag aattggcgaa cagactggat tattagatca gatgtcttac     300
ggtcgtttcg ttttaggttt atcagattgc gttaatgatt tcgaaatgga ttttttaaa     360 cgaaaacgta gttcacaaca acaacaattc gaagcatgtt atgaaatttt aaatgaagcc     420
ttaactacga attattgcca agcggatgat gattttttca attttccgag gatcagtgta    480
aatccccatt gtatctctga ggttaaacaa tacatttgg catcttctat gggtgtagtt    540
gaatgggccg ctcgaaaagg tcttccttta acgtatagat ggagtgatag tttagcagaa    600
aaagagaagt attatcagcg ttacttagcg gttgctaaag agaacaatat agatgtttca    660
aatatcgatc atcaatttcc tcttcttgta aatattaacg aaaatcgaag aatagcacga    720
gatgaagtac gtgagtacat tcagagttat gtatcagaag cctatcccac tgaccctaat    780
attgaacttc gtgtagaaga attgatcgaa caacacgcag tcgggaaagt cgatgaatat    840
tatgattcta cgatgcacgc tgtcaaagtt actggttcta aaaatttatt attatctttt    900
gaatctatga aaaataaaga tgacgtcact aaacttatca acatgttcaa ccaaaaaatc    960
aaggataact aataaagtg a                                                981

<210> SEQ ID NO 3
<211> LENGTH: 1437
<212> TYPE: DNA
<213> ORGANISM: Artificial Sequence
<220> FEATURE:
<223> OTHER INFORMATION: Synthesized

<400> SEQUENCE: 3
atgatcaaaa aaatccctat gataattggg ggagtagtcc agaacacatc cggttatgga       60
atgagagaat taacattaaa caataataaa gttaacattc aattatcac acaaagtgat      120 gtagaagcta ttcaatctct aaatattgag aacaaattga caataaatca gattgtaaat     180

```
ttcctttata ctgtaggcca aaaatggaaa tctgagacgt atagtcgtcg attaacttat      240
atcagagatt taatcaaatt cttaggttat agtcaggaaa tggctaaatt ggaagctaat      300
tggattagta tgatattatg ttctaaaagt gctttatatg acatagtaga aaatgattta      360
agtagtcgtc atatcattga tgaatggatt ccccaaggtg aatgctatgt aaaagcattg      420
cctaagggta agtccgtaca cttgttagca ggaaatgttc ctttatcagg agtaacctcc      480
atactaagag caattcttac aaaaaatgaa tgcattatta aaactagttc agcagaccca      540
tttactgcca ctgcacttgt taactctttt atagacgttg atgccgaaca tcctataaca      600
cgatccatta gtgtaatgta ttggtcccat tctgaagatt tagcaattcc caaacaaata      660
atgtcttgtg ctgacgttgt tatagcatgg ggaggggacg atgcaataaa atgggcaact      720
gaacatgcac cttctcacgc agacatattg aaattcggac cgaaaaaatc catttccatt      780
gtcgataatc ctacggatat taaggcagct gctatcggag tggctcatga catttgtttt      840
tatgatcagc aagcatgctt ctcaacccaa gatatatatt atatcggaga ttcaattgat      900
attttctttg atgaattagc tcaacagtta aataaatata aagacatttt acctaaaggg      960
gaacgaaatt tcgatgagaa ggcagctttc tcccttactg aaagagagtg tcttttcgca     1020
aaatataaag ttcaaaaagg tgaatcccaa tcttggttgc ttacccaaag tccagcggga     1080
agttttggaa atcaaccttt gagtcgttct gcgtatattc atcaggtaaa tgatataagt     1140
gaagtaatac ccttcgtaca taaggagtt actcaaactg tagctatcgc gccttgggaa     1200 tcaagttttta aatacagaga tattttggct gagcatggtg ctgagcgtat cattgaagca     1260
ggaatgaata acattttttcg tgtaggaggt gcccacgatg ggatgcgacc cttgcaacgt     1320
ttggttaatt atatttctca tgaacgtcct agtacatata caacaaaaga tgttagtgta     1380
aaaatagaac agacaaggta tcttgaagaa gataaattct agttttttgt accgtag       1437
```

<210> SEQ ID NO 4
<211> LENGTH: 948
<212> TYPE: DNA
<213> ORGANISM: Artificial Sequence
<220> FEATURE:
<223> OTHER INFORMATION: Synthesized

<400> SEQUENCE: 4

```
atggaaaata cacaacatag tttacctatt gatcacgtaa tcgacatagg tgacaaccgt       60
tacatcaggg tgtgggaaac taaacctaaa aacaaagaaa ctaaagaaa taataccata      120 gtgatagcgt ccggttttgc aagaagaatg gatcactttg ctggattagc tgaatatctt      180
gccaacaatg gattccgagt tattagatac gattcactaa atcatgtggg cttgtctagt      240
ggtgaaatta aacagtttag tatgtctgta ggtaaacatt ctttgctaac ggtaattgat      300
tggcttaaag aacgaaatat caacaatatt ggactaattg caagttcctt aagtgcccgt      360
atagcctatg aagtagccgc agaaattgat ttatccttcc ttataacagc agttggggtt      420
gtgaatttac gttctactct tgaaaaagca cttaaatatg attatttgca gatggaagtc      480
aatacgattc ctgaagactt aatatttgaa gggcataatc taggttcaaa agttttttgtg      540 actgattgtt ttgaaaacaa ctgggattct ttagactcaa ctattaataa aatttgtgag      600
cttgatattc cgttcatagc tttcacttct gatggggatt attgggtttg tcaacatgaa      660
gtaaaacacc tagtgtccaa tgtaaaatct gacaaaaaaa agatatactc tttagttggt      720
agttcccatg atttggggga aaatttggtc gttttacgaa atttctatca agtatgact      780 aaagctgctg tctcattgga taggcaattg gttgaattag ttgatgaaat catagaacca      840
```

| | |
|---|---|
| aattttgagg atttaaccgt aattacagtc aatgaaagaa gacttaaaaa taaaatagaa | 900 |
| aatgaaataa taaacagact agcagatcga gttcttgctt ccgtataa | 948 |

<210> SEQ ID NO 5
<211> LENGTH: 1122
<212> TYPE: DNA
<213> ORGANISM: Artificial Sequence
<220> FEATURE:
<223> OTHER INFORMATION: Synthesized

<400> SEQUENCE: 5

| | |
|---|---|
| atgtccacct tactaaacat cgatgcaacg gagattaaag ttagtaccga gatagatgat | 60 |
| ataatcttta caagtagtcc attaacttta ttatttgaag atcaagaaaa aattcagaaa | 120 |
| gaattaatac ttgaaagttt tcattatcat tataaccata ataaagatta caagtattat | 180 |
| tgtaatattc aggggttga tgagaacatt caatcaattg acgacattcc agtatttcct | 240 |
| acatccatgt ttaaatactc tcgtcttcat acagccgatg agagtaatat agaaaattgg | 300 |
| tttacatcat ccggtactaa aggcgttaag tctcatattg ctagggatag gcagtcaatt | 360 |
| gaaagattac taggatcagt taattatggt atgaaatatc ttggagaatt tcatgaacat | 420 |
| caacttgaac ttgtaaatat gggaccagat cgttttttccg cttcaaacgt gtggttcaaa | 480 |
| tatgttatga gttagtagaa attgttatat cctactactt ttactgtgga aaatgatgag | 540 |
| atagattttg aacaaactat cttggcttta aaagcgatac aacgaaaagg aaaaggaata | 600 |
| tgtttaatag gaccgcctta ttttatatac ttgttatgcc attatatgaa agaacataat | 660 |
| atagaattta atgcaggggc tcacatgttt attattacgg gagggggatg gaaaacaaaa | 720 |
| caaaagagg cgttaaatag gcaagatttc aatcaacttc ttatggaaac attctcctta | 780 |
| tttcatgagt cacaaattag agacatattt aatcaagttg aattgaatac atgtttcttc | 840 |
| gaagattctc ttcaacgaaa acatgtgcca ccttgggtat atgctcgtgc attagatcct | 900 |
| gttactttga ctcccgtaga agacgggcag gaaggcttga tgtcttatat ggacgcctcc | 960 |
| agtacatcat atccgacttt catcgttacg gatgatattg gcattgtaag gcatctaaaa | 1020 |
| gagccagatc ccttccaagg tacaaccgta gaaattgtta gacgtcttaa cacacgagag | 1080 |
| caaaagggtt gttctttatc tatggctaca agtcttaaat aa | 1122 |

<210> SEQ ID NO 6
<211> LENGTH: 705
<212> TYPE: DNA
<213> ORGANISM: Artificial Sequence
<220> FEATURE:
<223> OTHER INFORMATION: Synthesized

<400> SEQUENCE: 6

| | |
|---|---|
| atgatcttca actgtaaagt caaaaaagtt gaagcatccg attcacatat ttataaagtc | 60 |
| tttatcaaac ccgataagtg tttcgatttt aaagcaggcc aatatgttat tgtgtaccta | 120 |
| aacgggaaaa atttaccatt tagtatagcc aactgtccta catgtaatga attattggaa | 180 |
| ttacatgtag gcgggtctgt aaagaatct gcaattgaag caatatcaca ctttattaat | 240 |
| gcttttatat atcaaaaaga atttactatt gatgctccgc atggagacgc ctggttacga | 300 |
| gatgagtctc aatctccgct tttgttaata gctggcggca caggtttatc atatatcaat | 360 |
| agtatttaa gttgctgcat ttctaaacaa ctatcccaac cgatctattt atactggggt | 420 |
| gtcaacaatt gtaaccttt gtatgcagat caacaattaa aaactttggc cgcacaatat | 480 |
| cgtaatatta attatatccc tgtagttgag atcttaata cagattggca aggaaaaatt | 540 |

```
gggaatgtaa tagatgcagt aatcgaagat tttagtgacc tttcagattt cgacatctat      600
gtttgtggac ccttcggtat gtccagaaca gctaaagata ttctaatttc acaaaagaaa      660
gcaaacatag ggaagatgta ttcagatgct tttctttaca cgtga                     705
```

<210> SEQ ID NO 7
<211> LENGTH: 702
<212> TYPE: DNA
<213> ORGANISM: Artificial Sequence
<220> FEATURE:
<223> OTHER INFORMATION: Synthesized

<400> SEQUENCE: 7

```
atgactactc tttcttgtaa ggtgacatca gtggaggcta taactgacac agtgtacaga       60
gttagaatcg taccagatgc agcatttagt tttagggccg gtcaatattt gatggttgta      120
atggacgaga gagataagag accattcagc atggcctcta ctccagatga aaagggtttt      180
atcgaactgc acattggagc atcagagatc aatttatacg caaaagcagt catggacagg      240
atcttaaagg accatcagat tgttgttgat attcctcacg gcgaagcatg gcttagggat      300
gatgaggaaa gacctatgat tctcatcgct ggcggaacag ggttctctta cgctaggtct      360
atactcctca ccgccctagc acgtaatcca aatagggata ttaccattta ctggggtggt      420
agagaagagc agcacccttta cgacctttgc gaattggagg cccttagctt aaagcatcct      480
ggtctacaag ttgtgccagt tgtcgaacaa cctgaggcag gatggagagg gcgtacagga      540
acagtgctaa ctgccgttttt acaggatcat ggcactcttg ctgagcacga tatttatatt      600
gccggtagat tcgaaatggc taagattgca cgtgaccttt tttgttctga agaaatgcc       660 agggaagata gattgttcgg tgatgctttc gcattcattt ga                        702
```

<210> SEQ ID NO 8
<211> LENGTH: 585
<212> TYPE: DNA
<213> ORGANISM: Artificial Sequence
<220> FEATURE:
<223> OTHER INFORMATION: Synthesized

<400> SEQUENCE: 8

```
atgtttaaag gaattgtgga aggcattgga atcattgaga agatagacat atatacagac       60
cttgacaagt atgccatcag attccctgaa aacatgttga acggcattaa aaaagagtct      120
tccattatgt ttaacggctg cttttcttaca gtgaccagcg ttaatagcaa catcgtctgg      180
tttgatattt tgagaagga agctaggaaa ctggatacat ttagagaata aaggttgga       240 gatagagtca atttgggtac attcccaaag tttggtgctg catctggagg acatattttg      300
agtgcaagaa tatcttgcgt tgctagtatt attgagatta tagagaatga agattatcaa      360
cagatgtgga ttcagattcc tgagaacttt actgagttct taattgacaa agactatatt      420
gctgtcgatg gtatctcttt aacaatcgac actataaaaa acaatcagtt ttttattagt      480
ttgccgttaa aaatagctca aaataccaac atgaaatgga ggaaaaaggg agataaggtt      540
aacgtggagt tgtctaataa gattaacgct aatcagtgtt ggtga                     585
```

<210> SEQ ID NO 9
<211> LENGTH: 478
<212> TYPE: PRT
<213> ORGANISM: Photobacterium leiognathi

<400> SEQUENCE: 9

```
Met Ile Lys Lys Ile Pro Met Ile Ile Gly Gly Val Val Gln Asn Thr
1               5                   10                  15
```

```
Ser Gly Tyr Gly Met Arg Glu Leu Thr Leu Asn Asn Asn Lys Val Asn
            20                  25                  30

Ile Pro Ile Ile Thr Gln Ser Asp Val Glu Ala Ile Gln Ser Leu Asn
        35                  40                  45

Ile Glu Asn Lys Leu Thr Ile Asn Gln Ile Val Asn Phe Leu Tyr Thr
50                  55                  60

Val Gly Gln Lys Trp Lys Ser Glu Thr Tyr Ser Arg Arg Leu Thr Tyr
65                  70                  75                  80

Ile Arg Asp Leu Ile Lys Phe Leu Gly Tyr Ser Gln Glu Met Ala Lys
                85                  90                  95

Leu Glu Ala Asn Trp Ile Ser Met Ile Leu Cys Ser Lys Ser Ala Leu
            100                 105                 110

Tyr Asp Ile Val Glu Asn Asp Leu Ser Ser Arg His Ile Ile Asp Glu
        115                 120                 125

Trp Ile Pro Gln Gly Glu Cys Tyr Val Lys Ala Leu Pro Lys Gly Lys
130                 135                 140

Ser Val His Leu Leu Ala Gly Asn Val Pro Leu Ser Gly Val Thr Ser
145                 150                 155                 160

Ile Leu Arg Ala Ile Leu Thr Lys Asn Glu Cys Ile Ile Lys Thr Ser
                165                 170                 175

Ser Ala Asp Pro Phe Thr Ala Thr Ala Leu Val Asn Ser Phe Ile Asp
            180                 185                 190

Val Asp Ala Glu His Pro Ile Thr Arg Ser Ile Ser Val Met Tyr Trp
        195                 200                 205

Ser His Ser Glu Asp Leu Ala Ile Pro Lys Gln Ile Met Ser Cys Ala
210                 215                 220

Asp Val Val Ile Ala Trp Gly Gly Asp Ala Ile Lys Trp Ala Thr
225                 230                 235                 240

Glu His Ala Pro Ser His Ala Asp Ile Leu Lys Phe Gly Pro Lys Lys
            245                 250                 255

Ser Ile Ser Ile Val Asp Asn Pro Thr Asp Ile Lys Ala Ala Ala Ile
        260                 265                 270

Gly Val Ala His Asp Ile Cys Phe Tyr Asp Gln Gln Ala Cys Phe Ser
275                 280                 285

Thr Gln Asp Ile Tyr Tyr Ile Gly Asp Ser Ile Asp Ile Phe Phe Asp
290                 295                 300

Glu Leu Ala Gln Gln Leu Asn Lys Tyr Lys Asp Ile Leu Pro Lys Gly
305                 310                 315                 320

Glu Arg Asn Phe Asp Glu Lys Ala Ala Phe Ser Leu Thr Glu Arg Glu
                325                 330                 335

Cys Leu Phe Ala Lys Tyr Lys Val Gln Lys Gly Glu Ser Gln Ser Trp
            340                 345                 350

Leu Leu Thr Gln Ser Pro Ala Gly Ser Phe Gly Asn Gln Pro Leu Ser
        355                 360                 365

Arg Ser Ala Tyr Ile His Gln Val Asn Asp Ile Ser Glu Val Ile Pro
370                 375                 380

Phe Val His Lys Ala Val Thr Gln Thr Val Ala Ile Ala Pro Trp Glu
385                 390                 395                 400

Ser Ser Phe Lys Tyr Arg Asp Ile Leu Ala Glu His Gly Ala Glu Arg
                405                 410                 415

Ile Ile Glu Ala Gly Met Asn Asn Ile Phe Arg Val Gly Gly Ala His
            420                 425                 430

Asp Gly Met Arg Pro Leu Gln Arg Leu Val Asn Tyr Ile Ser His Glu
```

```
                435           440           445
Arg Pro Ser Thr Tyr Thr Thr Lys Asp Val Ser Val Lys Ile Glu Gln
450                 455                 460

Thr Arg Tyr Leu Glu Glu Asp Lys Phe Leu Val Phe Val Pro
465                 470                 475

<210> SEQ ID NO 10
<211> LENGTH: 373
<212> TYPE: PRT
<213> ORGANISM: Photobacterium leiognathi

<400> SEQUENCE: 10

Met Ser Thr Leu Leu Asn Ile Asp Ala Thr Glu Ile Lys Val Ser Thr
1               5                   10                  15

Glu Ile Asp Asp Ile Ile Phe Thr Ser Ser Pro Leu Thr Leu Leu Phe
                20                  25                  30

Glu Asp Gln Glu Lys Ile Gln Lys Glu Leu Ile Leu Glu Ser Phe His
            35                  40                  45

Tyr His Tyr Asn His Asn Lys Asp Tyr Lys Tyr Tyr Cys Asn Ile Gln
        50                  55                  60

Gly Val Asp Glu Asn Ile Gln Ser Ile Asp Asp Ile Pro Val Phe Pro
65                  70                  75                  80

Thr Ser Met Phe Lys Tyr Ser Arg Leu His Thr Ala Asp Glu Ser Asn
                85                  90                  95

Ile Glu Asn Trp Phe Thr Ser Ser Gly Thr Lys Gly Val Lys Ser His
            100                 105                 110

Ile Ala Arg Asp Arg Gln Ser Ile Glu Arg Leu Leu Gly Ser Val Asn
        115                 120                 125

Tyr Gly Met Lys Tyr Leu Gly Glu Phe His Glu His Gln Leu Glu Leu
130                 135                 140

Val Asn Met Gly Pro Asp Arg Phe Ser Ala Ser Asn Val Trp Phe Lys
145                 150                 155                 160

Tyr Val Met Ser Leu Val Gln Leu Leu Tyr Pro Thr Thr Phe Thr Val
                165                 170                 175

Glu Asn Asp Glu Ile Asp Phe Glu Gln Thr Ile Leu Ala Leu Lys Ala
            180                 185                 190

Ile Gln Arg Lys Gly Lys Gly Ile Cys Leu Ile Gly Pro Pro Tyr Phe
        195                 200                 205

Ile Tyr Leu Leu Cys His Tyr Met Lys Glu His Asn Ile Glu Phe Asn
210                 215                 220

Ala Gly Ala His Met Phe Ile Ile Thr Gly Gly Trp Lys Thr Lys
225                 230                 235                 240

Gln Lys Glu Ala Leu Asn Arg Gln Asp Phe Asn Gln Leu Leu Met Glu
                245                 250                 255

Thr Phe Ser Leu Phe His Glu Ser Gln Ile Arg Asp Ile Phe Asn Gln
            260                 265                 270

Val Glu Leu Asn Thr Cys Phe Phe Glu Asp Ser Leu Gln Arg Lys His
        275                 280                 285

Val Pro Pro Trp Val Tyr Ala Arg Ala Leu Asp Pro Val Thr Leu Thr
290                 295                 300

Pro Val Glu Asp Gly Gln Glu Gly Leu Met Ser Tyr Met Asp Ala Ser
305                 310                 315                 320

Ser Thr Ser Tyr Pro Thr Phe Ile Val Thr Asp Asp Ile Gly Ile Val
                325                 330                 335

Arg His Leu Lys Glu Pro Asp Pro Phe Gln Gly Thr Thr Val Glu Ile
```

```
            340             345             350
Val Arg Arg Leu Asn Thr Arg Glu Gln Lys Gly Cys Ser Leu Ser Met
        355                 360                 365

Ala Thr Ser Leu Lys
        370

<210> SEQ ID NO 11
<211> LENGTH: 1437
<212> TYPE: DNA
<213> ORGANISM: Artificial Sequence
<220> FEATURE:
<223> OTHER INFORMATION: Synthesized

<400> SEQUENCE: 11
atgatcaaaa aaatccctat gataattggg ggagtagtcc agaacacatc cggttatgga      60
atgagagaat taacattaaa caataataaa gttaacattc caattatcac acaaagtgat     120
gtagaagcta ttcaatctct aaatattgag aacaaattga caataaatca gattgtaaat     180
ttcctttata ctgtaggcca aaaatggaaa tctgagacgt atagtcgtcg attaacttat     240
atcagagatt taatcaaatt cttaggttat agtcaggaaa tggctaaatt ggaagctaat     300
tggattagta tgatattatg ttctaaaagt gctttatatg acatagtaga aaatgattta     360
agtagtcgtc atatcattga tgaatggatt ccccaaggtg aatgctatgt aaaagcattg     420
cctaagggta agtccgtaca cttgttagca ggaaatgttc ctttatcagg agtaacctcc     480
atactaagag caattcttac aaaaaatgaa tgcattatta aaactagttc agcagaccca     540
tttactgcca ctgcacttgt taactctttt atagacgttg atgccgaaca tcctataaca     600
cgatccatta gtgtaatgta ttggtcccat tctgaagatt tagcaattcc caaacaaata     660
atgtcttgtg ctgacgttgt tatagcatgg ggaggggacg atgcaataaa atgggcaact     720
gaacatgcac cttctcacgc agacatattg aaattcggac cgaaaaaatc catttccatt     780
gtcgataatc tacggatat taaggcagct gctatcggag tggctcatga catttgtttt     840
tatgatcagc aagcatgctt ctcaacccaa gatatatatt atatcggaga ttcaattgat     900
attttctttg atgaattagc tcaacagtta aataaatata agacatttt acctaaaggg     960 gaacgaaatt tcgatgagaa ggcagctttc tcccttactg aaagagagtg tcttttcgca    1020
aaatataaag ttcaaaaagg tgaatcccaa tcttggttgc ttacccaaag tccagcggga    1080
agttttggaa atcaaccttt gagtcgttct gcgtatattc atcaggtaaa tgatataagt    1140
gaagtaatac ccttcgtaca taaagcagtt actcaaactg tagctatcgc gccttgggaa    1200
tcaagtttta aatacagaga tattttggct gagcatggtg ctgagcgtat cattgaagca    1260
ggaatgaata cattttttcg tgtaggaggt gcccacgatg ggatgcgacc cttgcaacgt    1320
ttggttaatt atatttctca tgaacgtcct agtacatata caacaaaaga tgttagtgta    1380
aaaatagaac agacaaggta tcttgaagaa gataaattct tagttttgt accgtag       1437

<210> SEQ ID NO 12
<211> LENGTH: 1122
<212> TYPE: DNA
<213> ORGANISM: Artificial Sequence
<220> FEATURE:
<223> OTHER INFORMATION: Synthesized

<400> SEQUENCE: 12
atgtccacct tactaaacat cgatgcaacg gagattaaag ttagtaccga gatagatgat      60
ataatcttta caagtagtcc attaacttta ttatttgaag atcaagaaaa aattcagaaa     120
```

-continued

```
gaattaatac ttgaaagttt tcattatcat tataaccata ataaagatta caagtattat      180
tgtaatattc aggggttga tgagaacatt caatcaattg acgacattcc agtatttcct       240
acatccatgt ttaaatactc tcgtcttcat acagccgatg agagtaatat agaaaattgg     300
tttacatcat ccggtactaa aggcgttaag tctcatattg ctagggatag gcagtcaatt    360
gaaagattac taggatcagt taattatggt atgaaatatc ttggagaatt tcatgaacat   420
caacttgaac ttgtaaatat gggaccagat cgtttttccg cttcaaacgt gtggttcaaa    480
tatgttatga gtttagtaca attgttatat cctactactt ttactgtgga aaatgatgag    540
atagattttg aacaaactat cttggcttta aaagcgatac aacgaaaagg aaaaggaata   600
tgtttaatag gaccgcctta ttttatatac ttgttatgcc attatatgaa agaacataat   660
atagaattta atgcaggggc tcacatgttt attattacgg gagggggatg gaaaacaaaa   720 caaaagagg cgttaaatag gcaagatttc aatcaacttc ttatggaaac attctcctta   780
tttcatgagt cacaaattag agacatattt aatcaagttg aattgaatac atgtttcttc    840
gaagattctc ttcaacgaaa acatgtgcca ccttgggtat atgctcgtgc attagatcct   900
gttactttga ctcccgtaga agacgggcag gaaggcttga tgtcttatat ggacgcctcc   960
agtacatcat atccgacttt catcgttacg gatgatattg gcattgtaag gcatctaaaa  1020
gagccagatc ccttccaagg tacaaccgta gaaattgtta gacgtcttaa cacacgagag 1080
caaaagggtt gttctttatc tatggctaca agtcttaaat aa                     1122
```